United States Patent
Horger et al.

(10) Patent No.: US 11,686,799 B2
(45) Date of Patent: Jun. 27, 2023

(54) METHOD AND APPARATUS FOR GENERATION OF COMBINED MAGNETIC RESONANCE IMAGES

(71) Applicant: Siemens Healthcare GmbH, Erlangen (DE)

(72) Inventors: Wilhelm Horger, Schwaig (DE); Dominik Paul, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 762 days.

(21) Appl. No.: 15/718,308

(22) Filed: Sep. 28, 2017

(65) Prior Publication Data
US 2018/0088199 A1    Mar. 29, 2018

(30) Foreign Application Priority Data
Sep. 28, 2016   (DE) .......................... 102016218715.5

(51) Int. Cl.
*G01R 33/56*    (2006.01)
*G06T 5/00*    (2006.01)
(Continued)

(52) U.S. Cl.
CPC .......... *G01R 33/5608* (2013.01); *A61B 5/004* (2013.01); *A61B 5/055* (2013.01);
(Continued)

(58) Field of Classification Search
CPC ............ G01R 33/5608; G01R 33/5659; G01R 33/34084; G01R 33/3415; G06T 5/003;
(Continued)

(56) References Cited

U.S. PATENT DOCUMENTS

| 6,957,098 B1* | 10/2005 | Hyde ..................... A61B 5/055 600/424 |
| 2009/0225934 A1* | 9/2009 | Hugg ..................... A61B 6/037 378/20 |

(Continued)

FOREIGN PATENT DOCUMENTS

| DE | 102010017432 A1 | 1/2011 |
| DE | 102010043370 A1 | 5/2012 |
| DE | 102010061977 A1 | 5/2012 |

OTHER PUBLICATIONS

Xu, Dan et al. "Sense Reconstruction With Inaccurate Sensitivity Functions: Effects and Remedies" Proceedinqs of the 26th Conference of the IEEE EMBS, San Francisco, USA, pp. 1112-1115, 2004.

*Primary Examiner* — Bill Thomson
*Assistant Examiner* — Aminah Asghar
(74) *Attorney, Agent, or Firm* — Banner & Witcoff Ltd.

(57) ABSTRACT

In a method and magnetic resonance (MR) apparatus for generating a combined MR image of an examination object, a first image data record of an examination object, generated from magnetic resonance data recorded with a first reception coil, is loaded into a computer. A second image data record of the examination object, generated from magnetic resonance data recorded with a second reception coil, wherein the first and the second reception coils are different reception coils, is also loaded into a computer. At least one interim image data record is generated by the computer by applying a mask function to the first and/or second image data record. An interim image data record is combined in the computer with the image data record to which no mask function was applied, or with the other interim image data record, to form a combined MR image.

9 Claims, 3 Drawing Sheets

(51) Int. Cl.
*A61B 5/055* (2006.01)
*G01R 33/34* (2006.01)
*G06T 5/50* (2006.01)
*G01R 33/3415* (2006.01)
*G01R 33/565* (2006.01)
*A61B 5/00* (2006.01)
*G06T 11/60* (2006.01)

(52) U.S. Cl.
CPC ...... *A61B 5/4255* (2013.01); *G01R 33/34084* (2013.01); *G01R 33/5659* (2013.01); *G06T 5/003* (2013.01); *G06T 5/50* (2013.01); *G06T 11/60* (2013.01); *A61B 2576/02* (2013.01); *G01R 33/3415* (2013.01); *G06T 2207/10068* (2013.01); *G06T 2207/10088* (2013.01); *G06T 2207/20221* (2013.01)

(58) Field of Classification Search
CPC . G06T 5/50; G06T 11/60; G06T 2207/10068; G06T 2207/10088; G06T 2207/20221; A61B 5/004; A61B 5/055; A61B 5/4255; A61B 2576/02
See application file for complete search history.

(56) References Cited

U.S. PATENT DOCUMENTS

| | | |
|---|---|---|
| 2010/0322488 A1 | 12/2010 | Virtue et al. |
| 2011/0020235 A1* | 1/2011 | Hurd ............... A61B 5/415 424/9.3 |
| 2011/0069175 A1* | 3/2011 | Mistretta ............ G06T 5/004 348/164 |
| 2012/0112751 A1 | 5/2012 | Littmann et al. |
| 2012/0133361 A1 | 5/2012 | Gross |
| 2012/0249143 A1 | 10/2012 | Umeda |
| 2012/0323118 A1* | 12/2012 | Menon Gopalakrishna ........ A61B 8/463 600/431 |
| 2013/0137968 A1 | 5/2013 | Reisman et al. |
| 2013/0154640 A1* | 6/2013 | Block ............... G01R 33/48 324/309 |
| 2015/0054505 A1* | 2/2015 | Wang ............... G01R 33/5611 324/309 |
| 2015/0121171 A1* | 4/2015 | Minzoni ............ G06F 11/1048 714/766 |
| 2015/0121172 A1* | 4/2015 | Minzoni ............ G06F 11/1076 714/766 |
| 2016/0025833 A1* | 1/2016 | Polimeni ............ G01R 33/5608 324/309 |
| 2017/0328974 A1* | 11/2017 | Sanchez Gonzalez ........ A61B 5/055 |

* cited by examiner

METHOD AND APPARATUS FOR GENERATION OF COMBINED MAGNETIC RESONANCE IMAGES

BACKGROUND OF THE INVENTION

Field of the Invention

The present invention concerns an improvement in the generation of combined magnetic resonance images from magnetic resonance images, which were individually created from magnetic resonance data was recorded using different reception coils.

Description of the Prior Art

Magnetic resonance (MR) technology is a known modality that can be used to generate images of the inside of an examination object. In simple terms, the examination object is to this end positioned in a magnetic resonance scanner in a strong, static, homogeneous constant basic magnetic field, also called a $B_0$ field, with field strengths of 0.2 Tesla to 7 Tesla and more, such that its nuclear spins are oriented along the constant magnetic field. To trigger nuclear spin resonances, radio-frequency (RF) excitation pulses are radiated into the examination object (also called $B_1$ field). The triggered nuclear spin resonances are measured as so-called k-space data, and on the basis thereof MR images are reconstructed or spectroscopy data is determined. For spatially encoding the measurement data, rapidly switched magnetic gradient fields are overlaid on the constant magnetic field. The recorded measurement data are digitized and stored in the form of complex numeric values in a k-space matrix. An associated MR image can be reconstructed from populated k-space matrix, for example by a multidimensional Fourier transform.

In current MR recording methods, often several RF reception coils are used to record (detect) the MR signals that produce the measurement data. Local coils, which can be arranged flexibly and directly on an examination object to be examined, are often used because of their high signal-to-noise ratios (SNR), and because they produce a generally good signal level in the areas in their immediate environment. However, the farther away from the local coil that an object to be imaged is situated, the worse its MR signals are detected (received), because the signal intensity reduces as the distance from the coil increases. As a result, artifacts, in particular ghost artifacts, can occur. Larger local coils, which are used, for example, for measurements across larger areas of the examination object, such as in the area of the spine, can be formed of several sub-coils (known as coil arrays) so as to be able to cover larger areas of the examination object. Also, such local coil arrays provide a good SNR in the covered areas and are particularly recommended for overview images. Body coils built into the magnetic resonance systems on a fixed basis have a significantly more homogeneous behavior compared to local coils, particularly a significantly more homogeneous $B_1$ field, in the measurement volume of the magnetic resonance system.

When image data records that have each been respectively created from magnetic resonance data recorded with different reception coils are combined into a combination image, artifacts, in particular aforementioned ghost artifacts, can occur in the combination image as a result of different signal characteristics of the reception coils that are used. This effect occurs frequently in the case of combination images that combine image data records for which the respective magnetic resonance data were recorded with reception coils with significantly different signal characteristics.

SUMMARY OF THE INVENTION

An object of the present invention is to avoid the known problems when generating combination images from image data records where the magnetic resonance data were recorded respectively with different reception coils.

A method according to the invention for generating a combined magnetic resonance image of an examination object in accordance with the invention has the following steps.

A first image data record of an examination object, generated from magnetic resonance data recorded with a first reception coil, is loaded into a computer.

A second image data record of the examination object, generated from magnetic resonance data recorded with a second reception coil, wherein the first and the second reception coils are different reception coils, is also loaded into a computer.

At least one interim image data record is generated by the computer by applying a mask function to the first and/or second image data record.

An interim image data record is combined in the computer with the image data record to which no mask function was applied, or with the other interim image data record, to form a combined MR image.

The combined MR image is provided from the computer as a data file for storage or display.

By applying at least one mask function to at least one of the image data records to be combined, the relevant areas can be highlighted in an image data record to be combined depending on the coil characteristics of the respective reception coils that are used, which areas, for example, have a particularly good SNR and/or signal level. Artifacts in the obtained combination images can thereby be avoided.

At least one of the reception coils used to record the magnetic resonance data that form the basis of one of the image data records according to the invention can also be a transmission/reception coil. The reception coil can therefore also be used to generate the measured echo signals.

A reception coil used to record the magnetic resonance data that form the basis of one of the image data records according to the invention can be a local coil, in particular an endorectal coil. As a result of the possibility of being arranged very close to or directly at the examination object to be examined, local coils have a particularly high signal strength and a high SNR in the areas close to the local coil. Among local coils, endorectal coils have particularly suitable coil characteristics as a result of their specially adapted design.

A reception coil used to record the magnetic resonance data that form the basis of one of the image data records according to the invention can also be a coil array. Coil arrays provide good overview images in larger areas of an examination object.

A reception coil used to record the magnetic resonance data that form the basis of one of the image data records according to the invention can also be a body coil. Body coils have a particularly homogeneous behavior.

A combination of image data records from two different reception coils can provide particularly informative combination images because, for example, an area of interest particularly well mapped by the local coil can be well represented in the combination image in its anatomical environment recorded using a reception coil suitable for larger areas. This makes, inter alia, orientation and positioning of the mapped objects easier. However, in the case of such a combination of image data records from two different reception coils, artifacts can occur due to the different characteristics of the reception coils used.

An inventive magnetic resonance apparatus has a scanner with a basic field magnet, a gradient coil arrangement, a radio-frequency antenna, and a control computer designed to implement the inventive method, with a masking/combining processor.

The present invention also encompasses a non-transitory, computer-readable data storage medium encoded with programming instructions (program code) that, when the storage medium is loaded into a control computer or computer system of a magnetic resonance apparatus, cause the computer or computer system to operate the magnetic resonance apparatus in order to implement any or all embodiments of the method in accordance with the invention, as described above.

The advantages and details described above with respect to the method apply as well to the magnetic resonance apparatus and the electronically readable data storage medium.

DESCRIPTION OF THE PREFERRED EMBODIMENTS

Figure 1:
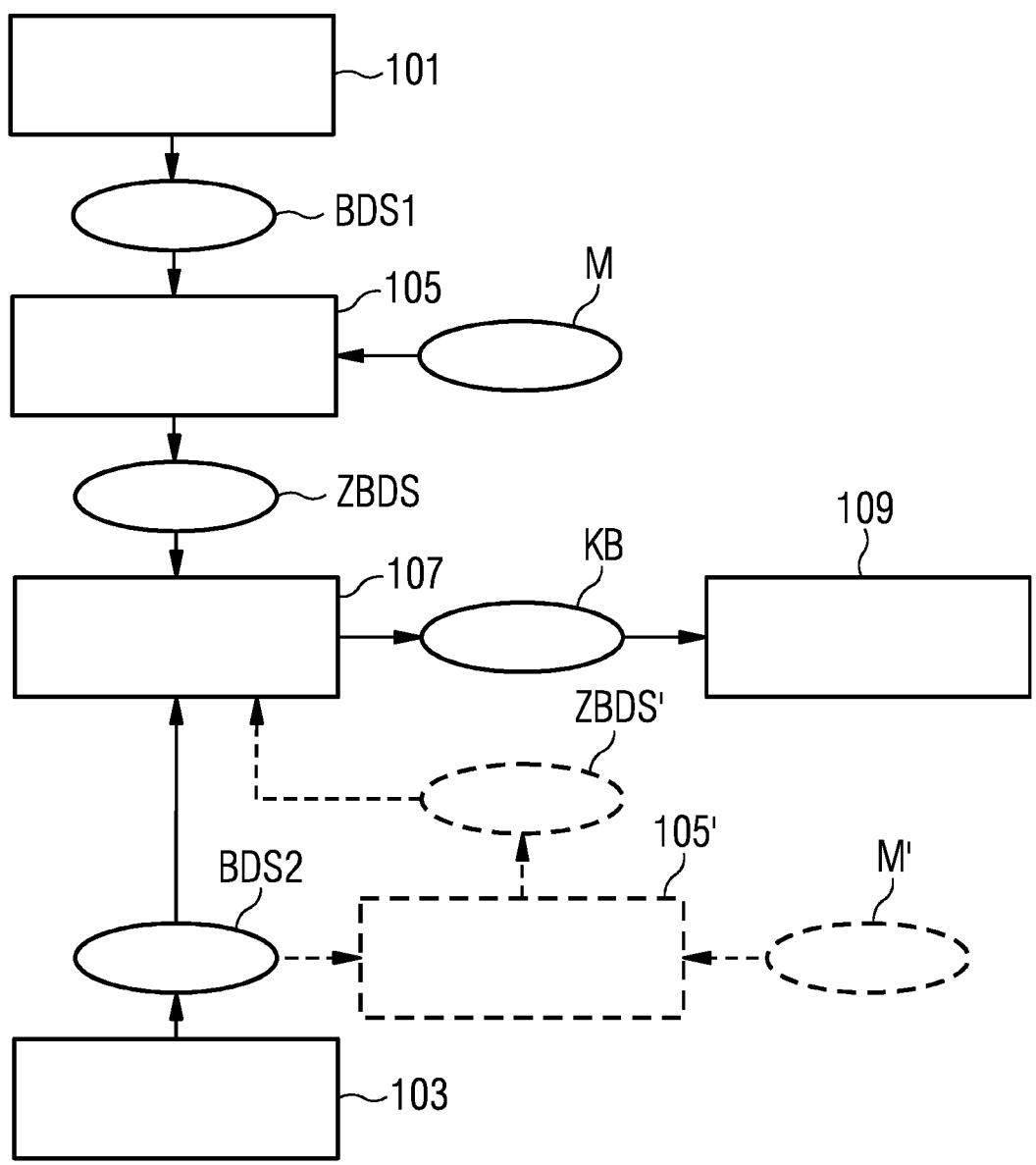
FIG. 1 is a flowchart of the method according to the invention.

FIG. 1 is a flowchart of the inventive method for generating a combined magnetic resonance image of an examination object.

A first image data record BDS1 of an examination object is loaded into a computer, this image data record having been generated from magnetic resonance data recorded using a first reception coil (Block 101).

A second image data record BDS2 of the examination object is also loaded into the computer, this image data record having been generated from magnetic resonance data recorded using a second reception coil, wherein the first and the second reception coil are different reception coils.

The first image data record BDS1 maps the same area of the examination object as the second image data record BDS2. The first image data record BDS1 and the second image data record BDS2 at least map the same object, e.g. organ or structure, of the examination object so that the first and the second image data record BDS1 and BDS2 can be combined such that this object is represented in the combined MR image.

A mask function is applied in the computer to at least one of the loaded image data records BDS1 or BDS2, to generate an interim image data record. In FIG. 1, for example, a mask function M is applied to the first image data record BDS1 to generate the interim image data record ZBDS (Block 105). It is also possible to apply a mask function M' to the second image data record BDS2 to generate a further interim image data record ZBDS' (Block 105'). In this way the respectively applied mask functions M and M' can be differentiated from one another. For example, the mask functions M, M' used can be adapted in each case to the reception coils used for recording the magnetic resonance data that forms the basis of the respective image data records. It is also possible for the mask function M' applied to the second image data record BDS2 to be a negative to the mask function M applied to the first image data record BDS1, e.g. to obtain the relevant information from the loaded image data records BDS1 and BDS2 in the combined MR image KB, this information being represented particularly well in the respective image data record BDS1 or BDS2.

If an interim image data record ZBDS is created from only one loaded image data record BDS1, this interim image data record ZBDS is combined with the other loaded image data record BDS2 to which no mask function was applied, in order to form a combined MR image KB (Block 107).

If mask functions M, M' are applied to both of the loaded image data records BDS1 and BDS2 and thus two interim image data records ZBDS, ZBDS' are created, these can be combined to form the combined MR image KB (Block 107).

The combination of the relevant image data records BDS1, BDS2, ZBDS, ZBDS' can for example include an addition of the image data records to be combined.

Combining the image data records (Block 107) can include a weighting of at least one of the image data records to be combined. In this way the portion of the respective image data records BDS1 and BDS2 in the combined MR image KB can be controlled.

The combined MR image KB can be saved and/or for example be displayed on a display device of a magnetic resonance system (Block 109).

The magnetic resonance data from which each of the first and the second image data records BDS1 and BDS2 were created can have been recorded at least partially at the same time using the different reception coils. As a result displacements caused by possible movements of the examination object in areas of the examination object mapped respectively in the image data records BDS1 and BDS2 are avoided or at least minimized.

Figure 2:
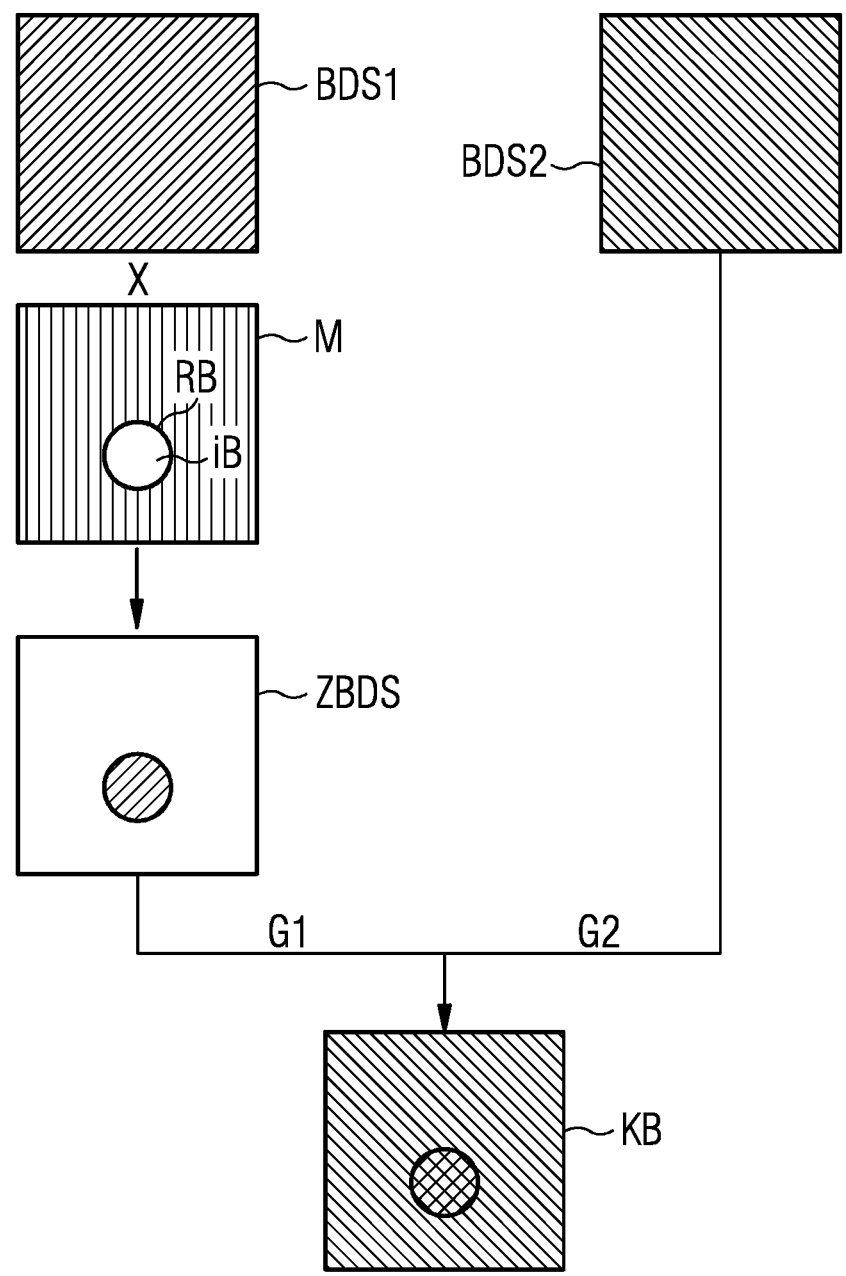
FIG. 2 is a schematic example of a combination image generated according to the invention.

FIG. 2 shows a schematic example of a combined MR image KB created according to the invention.

In the example shown a mask function M was applied to a first image data record BDS1 to obtain an interim image data record ZBDS.

The illustrated mask function M hides areas outside an area of interest iB so that only data within the area of interest iB is included in the interim image data record ZBDS. Here the edge of the area of interest can be precisely selected, i.e. all information outside of the area of interest iB is rejected and all information within the area of interest iB is retained.

It is also conceivable for the mask function M to gradually hide areas outside the area of interest iB via an edge area RB around the area of interest iB. In other words information in the edge area RB is subject to a desired gradual progression, weighted more and more weakly, by the mask function M, for example with increasing distance from a central area of the area of interest iB, and is only fully rejected outside the edge area RB. The size of the edge area RB, e.g. a distance from the outermost edge of the edge area to its internal edge flush with the area of interest iB, as well as a type of gradual hiding, can be selected depending on the mapped object and/or the coil characteristics of the reception coil used.

The area of interest iB can itself have a geometric form or a form determined with the aid of a segmentation method or a typical form loaded from a form database for an object mapped in the image data records BDS1, BDS2.

A geometric form, such as a circle, oval or rectangle, can be selected in such a way without any further actions so that an object included in the image data record BDS1, to which the mask function M is applied, remains in a desired way after application of the mask function M in the interim image data record ZBDS.

Determining the form of the area of interest iB with the aid of a segmentation method can be particularly well adjusted to an object contained in the image data record BDS1, wherein for example the segmentation method determines the form of the object and determines the area of interest iB on the basis of this determined form.

If the form of the area of interest iB is loaded as a typical form from a form database for an object mapped in the image data records BDS1, BDS2, a good adjustment of the form to the object can also be achieved. It is however then necessary to provide such a form database.

It is additionally or alternatively possible that the size of the area of interest iB depends on the size of the coil elements of the reception coil with which the magnetic resonance data was recorded, from which the image data record BDS1 or BDS2 was created, to which the mask function M is to be applied. Here, particular consideration can be given as to how large the sample area is for a reception coil used with a particularly high signal strength. For example, a size roughly two to three times the diameter of a coil element of the coil used can be selected to ensure a good signal intensity in the area of interest. In this way, dedicated mask functions can be formed for specific reception coils.

Precisely for reception coils that can only record magnetic resonance data with a good signal intensity and/or a good SNR in a limited area around the reception coil, such as for example endorectal coils, an application of a mask function on image data records created from magnetic resonance data recorded using the reception coil is to be recommended to avoid artifacts.

In the example shown in FIG. 2, the interim image data record ZBDS is now combined with the loaded second image data record BDS2 to form a combined MR image KB, in which all of the information from the second image data record BDS2, to which no mask function was applied, and the information of the first image data record BDS1 included in the interim image data record ZBDS in the area of interest iB, possibly with a gradual progression in the edge area RB, is included and combined. The interim image data record ZBDS can be weighted with a weighting factor G1 and/or the second image data record BDS2 with a weighting factor G2 to achieve a corresponding emphasis in the combined MR image KB.

Figure 3:
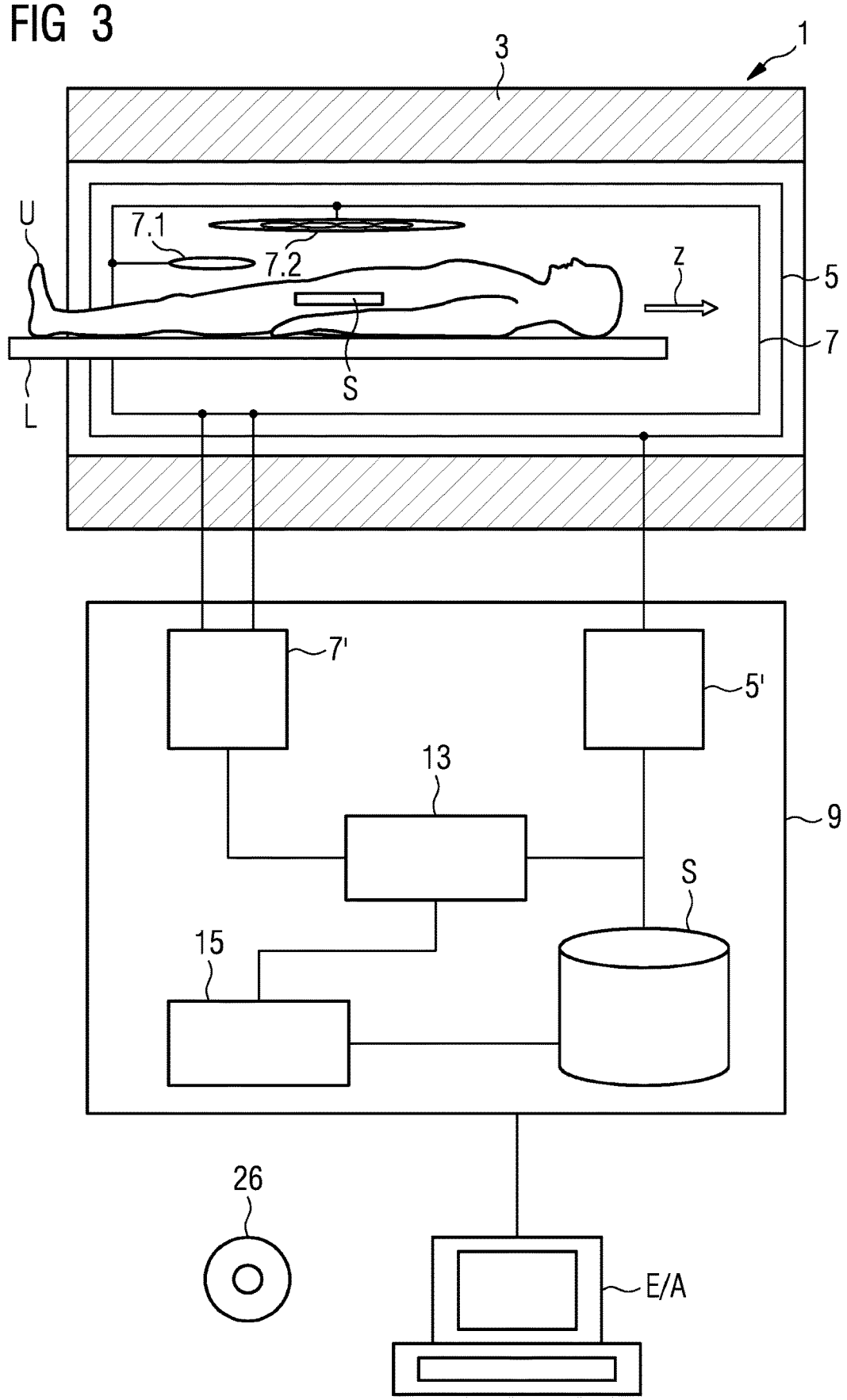
FIG. 3 schematically illustrates a magnetic resonance apparatus according to the invention.

FIG. 3 schematically shows an inventive magnetic resonance apparatus 1. This has a scanner with a magnet unit 3 that generates the constant basic magnetic field, a gradient coil arrangement 5 that generates the gradient fields, a radio-frequency antenna 7 for transmitting and receiving radio-frequency signals, and a control computer 9 designed for the performance of the inventive method. FIG. 3 schematically represents these subassemblies of the magnetic resonance apparatus 1 only roughly. In particular, the radio-frequency antenna 7 can be formed of several subunits, for example several coils like the schematically shown coils 7.1 and 7.2 or more coils, which can be designed either only to transmit radio-frequency signals or only to receive the triggered radio-frequency signals, or for both.

To examine an examination object U, for example a patient or a phantom, the examination object U can be introduced on a bed L into the scanner of the magnetic resonance apparatus 1, in the measurement volume thereof. The slice S represents an exemplary target volume of the examination object from which measurement data can be recorded.

The control computer 9 is used to control the magnetic resonance apparatus 1 and can in particular control the gradient coil arrangement 5 via a gradient controller 5' and the radio-frequency antenna 7 via a radio-frequency transmit/receive controller 7'. The radio-frequency antenna 7 can include several channels in which signals can be respectively sent or received.

The radio-frequency antenna 7 together with its radio-frequency transmit/receive controller 7' is responsible for generating and transmitting (sending) an alternating radio-frequency field so as to manipulate nuclear spins in an area to be manipulated (for example in slices S to be measured) of the examination object U and is also designed to operate local coils, e.g. also an endorectal coil, and a coil array 7.1, 7.2. The center frequency of the alternating radio-frequency field, also known as B1 field, must be close to the resonance frequency of the spins to be manipulated. To generate the B1 field, controlled currents are set at the RF coils in the radio-frequency antenna 7 using the radio-frequency transmit/receive controller 7'.

In addition, the control computer 9 has a masking/combining processor 15, with which image data records can be loaded and mask functions can be applied to image data records and image data records can be processed into combined combination images.

The control computer 9 is designed overall to implement a method according to the invention for avoiding artifacts during the acquisition of MR data of an examination object.

The processor 13 of the control computer 9 is designed to execute all processing operations needed for the requisite measurements and determinations. Interim results and results required for this purpose or determined in this connection can be stored in a memory M of the control computer 9. The units illustrated need not necessarily be physically separate units, but merely represent a categorization into functional units, which can also be implemented in fewer or in just one single physical unit.

Via an input/output device E/A of the magnetic resonance apparatus 1, it is possible for a user to enter control commands to the magnetic resonance apparatus 1 and/or to display results of the control computer 9 such as e.g. image data.

The method described herein can also exist in the form of program code stored on an electronically readable data storage medium 26. When the storage medium 26 is loaded in the control computer 9 of the magnetic resonance apparatus 1, the control computer 9 performs the method as described.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a combined magnetic resonance (MR) image of an examination object, comprising:
loading a first image data record of an examination object, generated from MR data recorded with a first reception coil, into a computer; loading a second image data record of the examination object into said computer, generated from MR data recorded with a second reception coil, the first reception coil and the second reception coil being different from each other, and the second reception coil having different coil characteristics than the first reception coil;

in said computer, generating one interim image data record by applying a mask function to the first image data record, wherein said mask function hides an area outside of an area of interest of the examination object, and a size of the area of interest depends on an area defined by the coil characteristics of the first or second reception coil with which the MR data were recorded and from which the respective image data record was created;

combining said one interim image data record in said computer with the second image data record to which no mask function was applied; and providing the combined MR image from the computer as a data file, formatted for storage or display.

2. The method as claimed in claim 1 wherein said first reception coil is a local coil.

3. The method as claimed in claim 1 wherein said first reception coil is an endorectal coil.

4. The method as claimed in claim 1 wherein said mask function gradually hides, in an edge region of said mask function, said areas outside of said area of interest of said examination object.

5. The method as claimed in claim 1 wherein said areas of interest have a geometric form, or a form determined by a segmentation method, or a form loaded from a data base.

6. The method as claimed in claim 1 wherein said second reception coil is a coil array.

7. The method as claimed in claim 1 comprising combining said image data records with a weighting of respective image data records that are combined with each other.

8. A magnetic resonance (MR) apparatus comprising:

an MR data acquisition scanner comprising a first reception coil and a second reception coil that are different from each other;

a computer loaded with a first image data record of an examination object, generated from MR data recorded with the first reception coil;

said computer also being loaded with a second image data record of the examination object, generated from MR data recorded with the second reception coil, wherein the second reception coil has different coil characteristics than the first reception coil;

said computer being configured to generate one interim image data record by applying a mask function to the first image data record, wherein said mask function hides an area outside of an area of interest of the examination object, and a size of the area of interest depends on an area defined by the coil characteristics of the first or second reception coil with which the MR data were recorded and from which the respective image data record was created;

said computer being configured to combine said one interim image data record in said computer with the second image data record to which no mask function was applied; and said computer being configured to provide the combined MR image from the computer as a data file, formatted for storage or display.

9. A non-transitory, computer-readable data storage medium encoded with programming instructions, said storage medium being loaded into a computer system of a magnetic resonance (MR) apparatus comprising first and second reception coils that are different from each other, said programming instructions causing said computer system to:

receive a first image data record of an examination object, generated from MR data recorded with the first reception coil;

receive a second image data record of the examination object, generated from MR data recorded with the second reception coil, the second reception coil having different coil characteristics than the first reception coil;

generate one interim image data record by applying a mask function to the first image data record, wherein said mask function hides an area outside of an area of interest of the examination object, and a size of the area of interest depends on an area defined by the coil characteristics of the first or second reception coil with which the MR data were recorded and from which the respective image data record was created;

combine said one interim image data record in said computer with the second image data record to which no mask function was applied; and provide the combined MR image from the computer system as a data file, formatted for storage or display.

* * * * *